(12) United States Patent
Erlandsson et al.

(10) Patent No.: US 11,161,321 B2
(45) Date of Patent: Nov. 2, 2021

(54) COMPOSITE ELASTIC NONWOVEN FABRIC

(71) Applicant: AVINTIV Specialty Materials Inc., Charlotte, NC (US)

(72) Inventors: Sven Krister Erlandsson, Advance, NC (US); Paul Michael Harmon, Troutman, NC (US); Philippe Guipouy, Colman (FR); Didier Hunsinger, Biesheim (FR); Robert Garcia Pano, Tarragona (ES); Gerard Baltzinger, Jebsheim (FR); Ralph A. Moody, III, Mooresville, NC (US)

(73) Assignee: AVINTIV Specialty Materials, Inc., Charlotte, NC (US)

( * ) Notice: Subject to any disclaimer, the term of this patent is extended or adjusted under 35 U.S.C. 154(b) by 503 days.

(21) Appl. No.: 15/000,732

(22) Filed: Jan. 19, 2016

(65) Prior Publication Data

US 2016/0207280 A1   Jul. 21, 2016

Related U.S. Application Data

(60) Provisional application No. 62/105,021, filed on Jan. 19, 2015.

(51) Int. Cl.
*B32B 5/26* (2006.01)
*B32B 5/04* (2006.01)
(Continued)

(52) U.S. Cl.
CPC .............. *B32B 5/26* (2013.01); *B32B 5/022* (2013.01); *B32B 5/04* (2013.01); *B32B 5/10* (2013.01);
(Continued)

(58) Field of Classification Search
None
See application file for complete search history.

(56) References Cited

U.S. PATENT DOCUMENTS

| 4,223,059 A | 9/1980 | Schwarz |
| 6,344,102 B1 | 2/2002 | Wagner |

(Continued)

FOREIGN PATENT DOCUMENTS

| EP | 0713546 A1 | 2/1995 |
| WO | 199504182 A1 | 2/1995 |

(Continued)

OTHER PUBLICATIONS

International Preliminary Report on Patentability of corresponding International Application No. PCT/US2016/013891 dated Jan. 12, 2017, all enclosed pages cited.

(Continued)

*Primary Examiner* — Shawn Mckinnon
(74) *Attorney, Agent, or Firm* — Burr & Forman LLP

(57) ABSTRACT

Elastic nonwoven composites suitable for a wide variety of uses are provided. The composite includes at least one extensible nonwoven layer, including a first extensible nonwoven layer, and at least one elastic nonwoven layer, in which the nonwoven layer comprises elastic continuous filaments. The composite may be bonded and activated by, at least in part, a stretching operation. The elastic continuous filaments may comprise an additive, such as a slip additive.

18 Claims, 8 Drawing Sheets

(51) Int. Cl.

| | | |
|---|---|---|
| *B32B 5/02* | (2006.01) | |
| *D06C 3/00* | (2006.01) | |
| *D04H 3/02* | (2006.01) | |
| *D04H 3/007* | (2012.01) | |
| *D04H 3/16* | (2006.01) | |
| *D04H 3/147* | (2012.01) | |
| *D04H 3/153* | (2012.01) | |
| *D04H 13/00* | (2006.01) | |
| *D04H 1/56* | (2006.01) | |
| *D04H 1/54* | (2012.01) | |
| *B32B 5/10* | (2006.01) | |
| *B32B 37/02* | (2006.01) | |
| *B32B 37/00* | (2006.01) | |
| *B32B 7/05* | (2019.01) | |

(52) U.S. Cl.
CPC ............ *B32B 7/05* (2019.01); *B32B 37/0053* (2013.01); *B32B 37/02* (2013.01); *D04H 1/54* (2013.01); *D04H 1/56* (2013.01); *D04H 3/007* (2013.01); *D04H 3/147* (2013.01); *D04H 3/153* (2013.01); *D04H 3/16* (2013.01); *D04H 13/00* (2013.01); *D06C 3/00* (2013.01); *B32B 2250/20* (2013.01); *B32B 2262/0215* (2013.01); *B32B 2262/0253* (2013.01); *B32B 2262/0261* (2013.01); *B32B 2262/0276* (2013.01); *B32B 2307/41* (2013.01); *B32B 2307/51* (2013.01); *B32B 2307/54* (2013.01); *B32B 2307/718* (2013.01); *B32B 2307/724* (2013.01); *B32B 2307/746* (2013.01); *B32B 2555/02* (2013.01); *D10B 2401/061* (2013.01)

(56) References Cited

U.S. PATENT DOCUMENTS

| | | | |
|---|---|---|---|
| 2005/0130544 A1* | 6/2005 | Cheng | B32B 5/022 |
| | | | 442/415 |
| 2006/0148358 A1* | 7/2006 | Hall | B32B 5/022 |
| | | | 442/328 |
| 2007/0141303 A1* | 6/2007 | Steindorf | B32B 27/12 |
| | | | 428/136 |
| 2009/0264038 A1* | 10/2009 | Boscolo | B32B 27/02 |
| | | | 442/329 |
| 2009/0324905 A1* | 12/2009 | Welch | B32B 7/05 |
| | | | 428/198 |
| 2010/0081352 A1 | 4/2010 | Westwood | |
| 2010/0222755 A1* | 9/2010 | Westwood | B32B 5/06 |
| | | | 604/358 |
| 2013/0239283 A1* | 9/2013 | Yokoyama | D01F 6/06 |
| | | | 2/9 |
| 2014/0276517 A1 | 9/2014 | Chester et al. | |

FOREIGN PATENT DOCUMENTS

| | | | |
|---|---|---|---|
| WO | 199917925 A1 | | 4/1999 |
| WO | 200038918 A1 | | 7/2000 |
| WO | WO0038918 | * | 7/2000 |

OTHER PUBLICATIONS

International Search Report and Written Opinion of corresponding application No. PCT/US2016/013891, dated Apr. 20, 2016, all enclosed pages cited.

* cited by examiner

COMPOSITE ELASTIC NONWOVEN FABRIC

CROSS-REFERENCE TO RELATED APPLICATIONS

This patent application claims the priority benefit of U.S. Provisional Application No. 62/105,021 filed on Jan. 19, 2015, the contents of which are incorporated herein by reference.

TECHNICAL FIELD

The invention provides elastic nonwoven composites and the process for the manufacture thereof. The elastic nonwoven composite fabrics are defined by multiple layers of continuous filaments with the filaments of the respective layers having defined elastomeric and/or extensible non-elastomeric extensible properties. The invention also provides a one step process for the manufacture of spunbond that may then be activated by an incremental stretching process to produce the composite elastic nonwoven fabrics of the invention.

BACKGROUND

There is an increasing demand for elastic and breathable nonwoven fabrics that can be economically manufactured while having desirable strength, conformability, and extensibility properties that are suitable for use in absorbent articles, such as disposable diapers, adult incontinence pads and sanitary napkins, and the like.

Conventionally, the elastic component of stretchable composites can be a significant contributor to the cost of the final product. Historically elastic films used in such composites had been made from expensive elastomeric products like styrenic block copolymers, polyurethanes or copolyester thermoplastic elastomers. Using a film as the core of a laminate also limits its breathability, which has required, in some cases, to develop apertures in the film. The process of imparting apertures to a film adds undesirable complexity and cost. Also, composites with a core made from an elastic film may have the tendency to be less drapability than otherwise required for certain end uses.

Conventionally, another approach has included using thermoplastic elastomeric polyolefins to make a meltblown layer with the meltblown layer being adhered to one or two layers of extensible nonwovens prior to being "activated" by incrementally stretching the composite. Thermoplastic elastomeric polyolefins may generally include lower cost elastomeric polymers, such as VISTAMAXX™ polymer, offered by ExxonMobil. The activation of the composite is generally achieved by a process that includes incremental stretching of the composite according to a ring roll process, for example. Examples of an incremental stretching process is described, for example, in U.S. Pat. Nos. 4,223,059 and 6,344,102 as well U.S. Publication No. 2014/0276517 (Ser. No. 14/206,699) incorporated herein by reference in their entirety.

Using an activated laminate/composite with an elastomeric thermoplastic polyolefin meltblown center layer is not ideal. It has been observed that the layer of meltblown filaments sometimes may become ruptured during activation, especially during more aggressive activation aimed at achieving a low load at 100% stretch, for example. Ruptures in the meltblown layer produce a non-uniform appearance when the laminate is stretched. These ruptures would likely be realized or perceived by a consumer as a defect as well as producing "micro strands" of the elastic component causing marks on a user's underlying skin.

An alternative approach to making an elastomeric meltblown layer has been to produce a layer of elastic continuous filaments having a sheath/core multicomponent structure by a spunbond process, in which the sheath or outside layer of the fiber is significantly less sticky than the core or inside layer. One issue with this approach, however, is that when a "non-sticky" material is used for the sheath, the filament is typically not elastomeric or is less elastomeric than desired, and it has been observed that the elastic properties of the filaments are typically undesirably reduced. Moreover, the sheaths can rupture and the filaments may still feel somewhat tacky to the user anyway as the surface of the elastomeric strand is exposed. Such an occurrence generally provides a less desirable hand to the fabric.

Therefore, there remains a need in the art for a nonwoven composite that exhibits desirably elasticity and may also be breathable, while exhibiting and producing desirable hand in term of softness, non-tackiness and drapability. Furthermore, there also remains a need for a simple process for economically making such elastic nonwoven composites.

SUMMARY OF INVENTION

One or more embodiments of the invention may address one or more of the aforementioned problems. Certain embodiments, according to the present disclosure, provide a nonwoven composite comprising at least one extensible nonwoven layer, in which the at least one extensible nonwoven layer includes a first extensible nonwoven layer. Composites according to some embodiments comprise at least one elastic nonwoven layer, in which the at least one elastic nonwoven layer comprises elastic continuous filaments (e.g., monofilaments). The composite according an embodiment of the invention may further comprises a second extensible nonwoven layer, in which the at least one elastic nonwoven layer is directly or indirectly positioned between the first extensible nonwoven layer and the second extensible nonwoven layer. In yet another embodiment, at least one of the first extensible nonwoven layer and the second extensible nonwoven layer comprises a continuous filament. In an embodiment of the invention, both the first extensible nonwoven layer and the second extensible nonwoven layer comprise continuous filaments and the at least one elastic nonwoven layer is at least mostly, preferably substantially devoid of non-continuous filaments. In certain further embodiments, at least one of the first extensible nonwoven layer and the second extensible nonwoven layer is substantially devoid of non-continuous filaments.

In certain embodiments of the invention, at least one of the first extensible nonwoven layer, the second extensible nonwoven layer, and the at least one elastic nonwoven layer comprise at least one polymeric material, such as at least one polyolefin material. In an embodiment, the at least one elastic nonwoven layer comprises an elastomeric polyolefin.

According to an embodiment of the invention, the composite comprises at least one elastic nonwoven layer comprising an additive, such as a slip additive. In an embodiment of the invention, at least a portion of the elastic continuous filaments of the at least one elastic nonwoven layer comprise a slip additive in an amount effective to reduce the tendency of the filaments to cling to process surfaces. In exemplary embodiments, for instance, the slip additive comprises from about 0.1 wt. % to about 10 wt. %, (e.g., 0.1-5 wt. %) based on the total weight of the elastic continuous filaments forming the at least one elastic nonwoven layer.

In an embodiment of the invention, at least one of the first extensible nonwoven layer and the second extensible nonwoven layer comprises substantially 100% extensible non-elastic filaments. In yet another embodiment, the first extensible nonwoven layer, the second extensible nonwoven layer, and the at least one elastic nonwoven layer are devoid of non-continuous filaments and/or a film.

In certain embodiments of the invention, the composite having a basis weight from about 40 to about 200 grams-per-square meter (gsm) or from about 70 to about 200 gsm. In an embodiment of the invention, the at least one elastic nonwoven layer comprises from about 25% to about 85% by weight of the composite or from about 40% to about 75% by weight of the composite. In an embodiment, the composite comprises a plurality of point bonds (e.g., thermally imparted point bonds). In certain embodiments, the composite comprises one or more layers that have been activated, in which the one or more activated layers comprises a first direction in which the one or more layers has been activated, at least in part, by an incremental stretching process. For example, the composite may comprise a Load Ratio in the first direction comprising less than about 30 (e.g., about 5 to about 20, about 5 to about 15, etc.).

In another aspect, the invention provides methods of making composites disclosed herein. In certain embodiments, methods may comprise forming a first extensible nonwoven layer comprising a first group of extensible filaments and depositing a plurality of elastic continuous filaments directly or indirectly onto the first extensible nonwoven layer to form an elastic nonwoven layer. The methods disclosed herein may also comprise depositing a second extensible nonwoven layer comprising a second group of extensible filaments directly or indirectly onto the elastic nonwoven layer to form the composite. Methods according to some embodiments of the invention may also comprise bonding (e.g., thermal bonding) the composite. In an embodiment, for example, the step of bonding the composite comprises forming a plurality of bonding points defining a bonded area, in which the bonded area comprises from about 2% to about 30% of an outer surface of the composite. In some embodiments of the invention, the methods comprise activating the composite to develop its elastic properties. The activating step may comprise at least partially stretching the composite in at least a first direction.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

DETAILED DESCRIPTION

Figure 1:
FIG. 1 illustrates a cross-sectional view of a nonwoven composite according to certain exemplary embodiments of the invention.

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Any relative dimensions illustrated in the figures are given by way of example and are not intended to be limiting. As would be appreciated by a person having ordinary skill in the art, the relative dimensions can vary depending on any number of factors including, without limitation, the intended use and performance of the illustrated article.

The invention includes, according to certain embodiments of the invention, a nonwoven composite comprising at least one extensible nonwoven layer and at least one elastic nonwoven layer, in which the at least one elastic nonwoven layer comprises elastic continuous filaments (e.g., monofilaments). In certain embodiments of the invention, the nonwoven composite may comprise a first extensible nonwoven layer, an elastic nonwoven layer, and a second extensible nonwoven layer, in which the elastic nonwoven layer may be directly or indirectly positioned between the two extensible layers. In this regard, certain embodiments of the invention may comprise two separate extensible outer layers made, for example, from continuous filaments and an elastic middle or interior layer made from elastic continuous filaments (e.g., monofilaments). Further pursuant to these embodiments of the invention, the first extensible nonwoven layer and/or the second extensible nonwoven layer may be substantially non-elastic.

The nonwoven composites, according to certain embodiments of the invention, may comprise one or more layers that have been activated, whereby, according to an embodiment of the invention, the one or more layers or, according to other embodiments of the invention, the composite has been bonded and subjected to an incremental stretching process to develop (or activate) its elastic properties. In certain embodiments of the invention, the elastic continuous filaments comprise an additive, such as a slip additive. The slip additive may be present in the elastic continuous filaments in an amount sufficient to reduce the stickiness and/or tendency of the filaments to adhere or stick to surfaces found in the process (e.g., a spunbond process). In certain embodiments of the invention, each of the layers (e.g., the extensible layers and the elastic nonwoven layer) may be spun simultaneously and thermal bonded into, for example, a spunbond nonwoven. As referenced above, the elastic properties of the nonwoven can be subsequently developed through activation, for example, by an incremental stretching process.

In certain embodiments of the invention, the composite may comprise an elastic nonwoven that comprises an activated nonwoven made from, for example, a spunbond process comprising, for example, three layers of continuous filaments made simultaneously. According to some embodiments of the invention, the middle or interior layer comprises elastic continuous filaments and the two outer layers comprise extensible non-elastic continuous filaments. In certain embodiments of the invention, the composite comprises multiple interior layers any of which or any combination of which may comprise elastic continuous filaments. The two outer layers between which the interior layers are disposed, according to an embodiment of the invention, may comprise extensible non-elastic continuous filaments.

The elastomeric thermoplastic filaments, according to another embodiment of the invention, may comprise one or several elastomeric thermoplastic polyolefin polymer.

The term "substantial" may encompass the whole amount as specified, according to certain embodiments of the invention, or largely but not the whole amount specified according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantiomers; and/or any chiral molecular configuration of such polymer or polymeric material. These configurations include, but are not limited to, isotactic, syndiotactic, and atactic configurations of such polymer or polymeric material.

The term "elastic", "elastomer" or "elastomeric", as used interchangeably herein, may comprise a material that when stretched and released will recover to near its original length (e.g., return to within 20%, 10%, 5%, 3%, or 1% of its original length). The term "elastic", "elastomer", or "elastomeric", as used interchangeably herein, may also comprise a material that exhibits the ability to be stretched and released several times and, to exert repetitively the same or just slightly lower force when stretched at the same extension level. Elastic materials, for example, may comprise elastomers, such as elastomeric polymers. Non-limiting exemplary elastomeric polymers may comprise, according to certain embodiments, elastomeric polyolefins (e.g., VISTAMAXX™ from ExxonMobil Chemical Company, VERSIFY™, a propylene-ethylene elastomeric polymer, and AFFINITY™ from The Dow Chemical Company), polyether block amide copolymer (e.g., PEBAX® from Arkema Group), polyester block amide copolymer, copolyester thermoplastic elastomer (e.g., ARNITEL® from DSM Engineering Plastics, HYTREL® from E.I. DuPont de Nemours and Company), thermoplastic urethane elastomer, and/or combinations thereof. In certain embodiments, exemplary elastomers may comprise VISTAMAXX™ propylene-based elastomers (commercially available form ExxonMobile), which comprise copolymers of propylene and ethylene. VISTAMAXX™ propylene-based elastomers, for example, comprise isotactic polypropylene microcrystalline regions and random amorphous regions.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process known in the art such as, for example, meltblowing processes, spunbonding processes, hydroentangling, air-laid, and bonded carded web processes.

The term "filament", as used herein, may comprise a fiber made from a formulation comprising a polymer (e.g., thermoplastic polymer(s)) that has been drawn and quenched with the intent of making a fiber with, for example, nearly infinite length as the process does not include a step of cutting it into pieces of a precise or discrete length such as the case for staple fibers. An example of a process that produces continuous filaments comprises spunbond processes. In certain embodiments, the process commonly identified as a meltblown process in not considered as producing continuous filaments since breaks in the fiber are common during the meltblown process.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous. It is noted that the spunbond used in certain composites of the invention may include nonwovens described in the literature as SPINLACE®.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Generally, meltblown fibers comprise microfibers that may be continuous or discontinuous. Meltblown fibers are generally tacky when deposited onto a collecting surface.

The term "layer", as used herein, may comprise a generally recognizable combination of similar material types and/or functions existing in the X-Y plane when other layers, if present, are disposed on one another through the Z plane.

The term "composite", as used herein, may comprise a structure comprising two or more layers, such as a plurality of layers of continuous filaments or even a plurality of nonwoven layers. Two layers of a composite structure may be joined together such that a substantial portion of their common X-Y plane interface, according to certain embodiments of the invention.

The term "machine direction" or "MD", as used herein, may comprise the direction of travel of the nonwoven web during manufacturing while the term "cross direction" or "CD", as used herein, refers to a direction that is perpendicular to the machine direction and extends laterally across the width of the nonwoven web.

The term "thermal point bonding", as used herein, may comprise a process involving passing a material such as one or more webs of fibers to be bonded between a heated patterned roll and an anvil roll. For example, the patterned roll may comprise a raised pattern of protrusions so that the fabric is bonded in discrete point bond sites rather than being bonded across its entire surface. Alternatively, "thermal point bonding" may comprise an ultrasonic bonding process using a patterned roll such as an anvil roll.

The term "extensible" and/or "extensible non-elastic" filaments or fabric, as used herein, may comprise filaments or fabrics which, upon application of a tensile stretching force can be stretched beyond its elastic limit and becomes permanently elongated and have little retractive force (e.g., non-elastic). Generally, extensible non-elastic materials may be substantially non-elastic and, by themselves, recover less than about 25% (e.g., less than about 20%, 15%, 10%, 5%, 3%, etc.) of their pre-elongated dimensions upon release of a tensile stretching force. "Extensible" and "extensible non-elastic" filaments or fabrics, in certain embodiments of the invention, may be activated or stretched with an incremental stretching unit (e.g., ring-roll apparatus) without catastrophic failure of the fibers. In one embodiment of the invention, for example, extensive filaments and/or fabrics may be stretched to 120% and even 150% or more in the direction of stretching.

The term "incremental stretching", as used herein, may comprise a process in which a web is supported at closely spaced apart locations and then the unsupported segments of the web between these closely spaced apart locations are stretched. A non-limiting example of incremental stretching rolls designed for machine direction and cross direction stretching can be found in U.S. Pat. No. 4,223,059, the contents of which are hereby incorporated herein by reference. Incremental stretching, according to one embodiment, may comprise a process performed by embossing of the web as illustrated in U.S. Patent Application No. 2014/0276517, the contents of which are hereby incorporated herein by reference.

The term "activated", as used herein, may comprise a material that has been mechanically deformed, for example by incremental stretching, in order to increase the extensibility of at least a portion of the material. In one embodiment, for example, a material (e.g., nonwoven web) may be activated by, for example, incrementally stretching the material in at least one direction.

I. Composite Elastic Nonwoven Fabric

In one aspect, the invention provides a nonwoven composite including at least one extensible nonwoven layer, including a first extensible nonwoven layer. The first extensible nonwoven layer, according to certain embodiments of the invention, may be substantially non-elastic. The composite further comprises at least one elastic nonwoven layer, in which the at least one elastic nonwoven layer comprises elastic continuous filaments. In certain embodiments, the at least one elastic nonwoven layer is devoid of non-continuous filaments. In certain embodiments, the composite may further comprise a second extensible nonwoven layer positioned such that the at least one elastic nonwoven layer is directly or indirectly positioned between the first extensible nonwoven layer and the second extensible nonwoven layer. The second extensible nonwoven layer, according to certain embodiments of the invention, may be substantially non-elastic. In one embodiment of the invention, the at least one elastic nonwoven layer consists of a single layer, while in other embodiments of the invention the at least one elastic nonwoven layer may comprise from two (2) to ten (10) discrete elastic nonwoven layers. Composites according to certain embodiments of the invention, for example, may comprise one or more elastic nonwoven layers directly or indirectly disposed between a first extensible nonwoven layer and a second extensible nonwoven layer.

Composites according to certain embodiments of the invention, may include a first extensible nonwoven layer and a second extensible nonwoven layer, in which at least one of the first or second extensible nonwoven layers comprise continuous filaments (e.g., extensible non-elastic filaments, according to certain embodiments of the invention). In an exemplary embodiment of the invention, both the first extensible nonwoven layer and the second extensible nonwoven layer comprise continuous filaments. In one embodiment of the invention, for example, the first extensible nonwoven layer and the second extensible nonwoven layer are each substantially devoid of non-continuous filaments. Additionally or alternatively, the first extensible nonwoven layer and/or the second extensible nonwoven layer are substantially devoid of elastic filaments. A composite, according to yet another exemplary embodiment of the invention, comprises at least one elastic nonwoven layer directly or directly disposed or positioned between the first and second extensible nonwoven layer, in which the composite is substantially devoid of non-continuous fibers (e.g., staple fibers, meltblown fibers, etc.). In this regard, such exemplary embodiment of the invention comprises a first extensible nonwoven and a second extensible nonwoven layer comprising substantially 100% (e.g., 95-100%) extensible non-elastic filaments, while the at least one elastic nonwoven layer comprises substantially 100% (e.g., 95-100%) continuous elastic monofilaments. In yet another embodiment of the invention, the composite may comprise a plurality of nonwoven layers, but be devoid of a film layer.

In certain embodiments of the invention, the filaments of the first extensible nonwoven layer, the second extensible nonwoven layer, and the at least one elastic nonwoven layer may each comprise at least one polymeric material. In certain embodiments of the invention, the at least one polymeric material comprises at least one polyolefin material. In one exemplary embodiment of the invention, each of the first extensible nonwoven layer, the second extensible nonwoven layer, and the at least one elastic nonwoven layer comprise at least one polyolefin. The at least one elastic nonwoven layer, in certain embodiments of the invention, may comprise at least one thermoplastic elastomeric polyolefin. In one embodiment of the invention, the at least one elastic nonwoven layer may comprise, consist, or consist essentially of at least one thermoplastic elastomeric polyolefin, while the first and second nonwoven layers may comprise filaments that are devoid of an elastomeric material (e.g., an elastomeric polyolefin).

Exemplary polymeric materials, suitable for certain embodiments of the invention, may comprise at least one of a polyolefin, a polyester, a polyamide, and/or any combination thereof. In some embodiments of the invention, for example, the polymer filaments (e.g., filaments of the extensible layers) may comprise at least one of polyethylene, polypropylene, partially aromatic or fully aromatic polyesters (e.g., polyethylene terephthalate), polyhexamethylene diadipamide, polycaprolactam, aromatic or partially aromatic polyamides, aliphatic polyamides, and/or combinations thereof. In other embodiments, for instance, the polymer filaments may comprise at least one of polypropylene, partially aromatic or fully aromatic polyesters (e.g., polyethylene terephthalate), and/or combinations thereof. In further embodiments of the invention, for example, the polymer filaments may comprise polypropylene. In other embodiments of the invention, for instance, the polymer filaments may comprise partially aromatic or fully aromatic polyesters (e.g., polyethylene terephthalate). In further embodiments of the invention, for example, the polymer filaments may comprise polyethylene terephthalate.

In accordance with certain embodiments of the invention, the first and/or second extensible nonwoven layers may comprise multi-component filaments. Further pursuant to this embodiment of the invention, the first and/or second extensible nonwoven layers may comprise bi-component filaments having, for example, a sheath-core structure. Multi-component filaments, however, may comprise a variety of additional configurations, such as side-by-side, segmented-pie, and islands-in-a-sea configurations. In certain embodiments of the invention, for example, sheath-core bi-component filaments may comprise a sheath comprising a first polymer (e.g., a polyolefin) and a core comprising a second polymer (e.g., a polyolefin), in which the first and second polymers are not the same. In some embodiments of the invention, for instance, the sheath may comprise at least one of a polyethylene or polypropylene. In further embodiments of the invention, for example, the sheath may comprise polyethylene. According to some embodiments of the invention, for instance, the core may comprise at least one of a polyolefin or polyester. In other embodiments of the invention, for example, the core may comprise at least one of polyethylene, polypropylene, polyester, and/or combinations thereof. In further embodiments of the invention, for instance, the core may comprise at least one of polypropylene or polyester.

According to certain embodiments of the invention, as referenced above, the at least one elastic nonwoven layer may comprise, consist, or consist essentially of at least one thermoplastic elastomeric material (e.g., a polyolefin). In some embodiments of the invention, exemplary elastomeric materials may include elastomeric polyolefins (e.g., VISTAMAXX™ from ExxonMobil Chemical Company, VERSIFY™ and AFFINITY™ from The Dow Chemical Company), polyether block amide copolymer (e.g., PEBAX® from Arkema Group), polyester block amide copolymer, copolyester thermoplastic elastomer (e.g., ARNITEL® from DSM Engineering Plastics, HYTREL® from E.I. DuPont de Nemours and Company), thermoplastic urethane elastomer, and/or combinations thereof. In certain embodiments, exemplary elastomers may comprise VISTAMAXX™ propylene-based elastomers (commercially available form ExxonMobile), which comprise copolymers of propylene and ethylene. VISTAMAXX™ propylene-based elastomers, for example, comprise isotactic polypropylene microcrystalline regions and random amorphous regions. In some embodiments of the invention, the elastic continuous filament may comprise other optional ingredients added to confer a desired functionality to the elastic continuous filaments. Such optional ingredients, for example, may comprise minor fractions of other polyolefins, pigments, antioxidants, and flame retardants, according to certain embodiments of the invention.

In certain embodiments of the invention, the elastic continuous filaments (e.g., monofilaments) of the of the at least one elastic nonwoven layer comprise one or more additives, such as pigments, antioxidants, flame retardant, and slip additives. For example, the elastic continuous filaments may comprise a slip additive. The slip additive may be topically applied to the elastic filaments and/or introduced to the elastomeric melt prior to melt-spinning the elastic continuous filaments. For instance, the slip additive(s) may be melt-dispersed in the elastomeric melt prior to melt-spinning. The incorporation of the slip additive may beneficially reduce the stickiness of the continuous elastic filaments against process surfaces associated with melt-spinning processes. The slip additive, for example, may beneficially reduce (or eliminate) the undesirable breakage of filaments and drips that may be associated with melt-spinning of an elastomeric material. In this regard, exemplary slip additives may bloom rapidly to the surface of the filaments and reduce their coefficient of friction against surfaces found in the process (e.g., wall of the diffuser section, walls of the draw unit, compression rolls, etc.), therefore allowing continuous production of the elastic nonwoven layer(s) with a minimum amount of defects due to break in the elastic continuous filaments.

Exemplary, but non-limiting examples of, slip additives according to certain embodiments of the invention, comprise one or more of the following: oleamide, erucamide, stearamide, ethylene-bis-oleamide, strearyl erucamide, oleyl palmitamide, bis-stearamide, epoxy functionalized polysiloxane, silicon compounds (e.g., silanes and silicone polymers, including silicone oils, polydiniethylsiloxane, amino-modified polydimethylsiloxane, etc.), and salt derivatives of aromatic or aliphatic hydrocarbon oils (e.g., metal salts of fatty acids, including calcium stearate, zinc stearate, etc.). However, any compound or compounds known to a person of ordinary skill in the art having the ability to migrate or bloom to the surface of a polymer as it is being processed may serve as a slip additive.

In certain embodiments of the invention, as noted above, the elastic continuous filaments of the at least one elastic nonwoven layer may comprise a slip additive in an amount effective to reduce the tendency of the elastic continuous filaments to cling to process surfaces. In some exemplary embodiments of the invention, for instance, the elastic continuous filaments may comprise a slip additive(s) comprising from about 0.1 wt. % to about 10 wt. %, based on the total weight of the elastic continuous filaments forming the at least one elastic nonwoven layer. In an embodiment of the invention, the elastic continuous filaments may comprise a slip additive(s) comprising from about 0.1 wt. % to about 5 wt. %, based on the total weight of the elastic continuous filaments forming the at least one elastic nonwoven layer. In certain embodiments of the invention, the elastic continuous filaments may comprise a slip additive(s) comprising from at least about any of the following: 0.05, 0.1, 0.2, 0.3, 0.5, 1, and 2 wt. % and/or at most about 20, 15, 12, 10, 9, 8, 7, 6, and 5 wt. % (e.g., 0.1-2 wt. %, 1-20%, etc.) based on the total weight of the elastic continuous filaments forming the at least one elastic nonwoven layer.

Composites in accordance with certain embodiments of the invention may comprise a basis weight of least about 20 grams-per-meter-squared (gsm), 30 gsm, or 40 gsm. In certain embodiments, the basis weight of the composite may comprise at least about any of the following: 20, 25, 30, 35, 40, and 45 gsm and/or at most about 200, 180, 150, 120, 100, and 70 gsm (e.g., 40-200 gsm, 70-200 gsm, etc.).

In accordance with certain embodiments of the invention, the at least one elastic nonwoven layer comprises from about 25% to about 85% by weight of the composite or from about 40% to about 75% by weight of the composite. In certain embodiments, the at least one elastic nonwoven layer comprises at least about any of the following: 20, 25, 30, 35, 40, and 45% by weight of the composite and/or at most about 90, 85, 75, 60, and 50% by weight of the composite (e.g., 20-90% by weight of the composite, 50-85% by weight of the composite, etc.).

As referenced above, composites, according to certain embodiments of the invention, comprise one or more layers that have been activated, in which the such one or more layers comprise a first direction in which the layer has been activated, at least in part, by a stretching process, such as an incremental stretching process, for example. During the activation process, the layer of elastic continuous filaments as well as the filaments of the extensible non-elastic layer(s) also become stretched, however due to the elastic nature the elastic continuous filaments they recover to be close to their original dimensions. Further pursuant to this embodiment of the invention, composites according to some embodiments may comprise a Load Ratio in a first direction comprising less than about 30. In one embodiment of the invention, the composite comprises a Load Ratio comprising from about 5 to about 20 or about 5 to about 15. In certain embodiments of the invention, the composite comprises a Load Ratio in at least a first direction of at least about any of the following: 1, 3, 5, 7, 10, and 15 and/or at most about 35, 30, 25, 20, and 15 (e.g., 3-15, 10-15, 1-30, etc.).

In accordance with certain embodiments of the invention, the composite may comprise a composite that has been bonded. For example, the composite may comprise a plurality of point bonds, which may be formed by a thermal bonding process. For example, the composite may be thermally bonded prior to being activated by, for example, using an incremental stretching process. In one embodiment of the invention, the plurality of point bonds may be imparted with a calender comprising a heated smooth or anvil roll and another heated roll with a raised pattern, in which the pattern comprises a plurality of protrusions that define a bonding area. The bonding area, for example, may comprise from 5 to 25% or 8 to 20% of the nonwoven composite surface.

FIG. 1 illustrates a cross-sectional view of a nonwoven composite according to certain exemplary embodiments of the invention. As shown in FIG. 1, the composite 10 may comprise a first extensible nonwoven layer 20, a second extensible nonwoven layer 24, and an elastic nonwoven layer 30, in which the elastic nonwoven layer is directly disposed between the first and second extensible layers.

II. Methods of Manufacturing a Composite Elastic Nonwoven Fabric

In another aspect, certain embodiments of the invention provide a method for producing a nonwoven composite disclosed herein. Methods according to some embodiments of the invention, for example, comprise forming a first extensible nonwoven layer comprising a first group of extensible filaments and depositing a plurality of elastic continuous filaments directly or indirectly onto the first extensible nonwoven layer to form an elastic nonwoven layer. In certain embodiments, the method may comprise depositing a second extensible nonwoven layer comprising a second group of extensible filaments directly or indirectly onto the elastic nonwoven layer to form a composite. In certain embodiments, the elastic nonwoven layer comprising elastic continuous filaments may be prepared separately from the first and/or second extensible nonwoven layers. In such embodiments, for instance, the elastic nonwoven layer or layers may be subsequently joined (e.g., bonded) to the first and/or second extensible layers. In one embodiment, for example, an elastic nonwoven layer comprising continuous elastic filaments can be provided or obtained as a stand-alone nonwoven material and disposed between the first and second extensible nonwoven layers. As discussed below, the assembled composite may also be bonded (e.g., thermally bonded) and/or activated to impart elastic properties to the composite.

Methods, according to certain embodiments, may comprise bonding the composite. Although the manner in which bonding of the composite occurs is not particularly limited, certain embodiments comprise thermally bonding the composite. For example, the composite may be thermally point bonded in which a plurality of point bonds may be imparted with a calender comprising a heated smooth or anvil roll and another heated roll with a raised pattern, in which the pattern comprises a plurality of protrusions that define a bonding area. The bonding area, for example, may comprise from about 2 to about 30%, from about 5 to 25%, or from about 8 to 20% of the nonwoven composite surface.

In accordance with certain embodiments, the method may also comprise activating the composite to develop its elastic properties. In certain embodiment, for example, the composite comprises a first direction in which the composite may be subjected to a stretching process, such as an incremental stretching process, to provide an activated composite exhibiting elastic properties. During the activation process, the layer of elastic continuous filaments as well as the filaments of the extensible non-elastic layer(s) also get stretched, however due to the elastic nature the elastic continuous filaments they recover to be close to their original dimensions. Activation of the composite, according to certain embodiments, may generally comprise a process including incremental stretching of the composite according to a ring roll process. An example an incremental stretching process is described, for example, in U.S. Pat. Nos. 4,223, 059 and 6,344,102 as well U.S. Publication No. 2014/0276517 (Ser. No. 14/206,699), the contents of each are hereby incorporated by reference. In this regard, composites according to some embodiments may comprise a Load Ratio in the first direction comprising less than about 30. In one embodiment, the composite comprises a Load Ratio comprising from about 5 to about 20, or about 5 to about 15. In certain embodiments, the composite comprises a Load Ratio in at least a first direction of at least about any of the following: 1, 3, 5, 7, 10, and 15 and/or at most about 35, 30, 25, 20, and 15 (e.g., 3-15, 10-15, 1-30, etc.).

Methods according to certain embodiments may also comprise forming an elastomeric-polymer melt and melt-spinning the elastomeric-polymer melt to form the plurality of elastic continuous filaments. In certain embodiments, the melt-spinning process comprises a spunbond process. In yet another embodiment, the extensible nonwoven layer(s) may also comprise a plurality of spunbond filaments.

In certain embodiments of the invention, the elastic continuous filaments (e.g., monofilaments) produced, for example, by a melt-spinning process comprise one or more additives, such as pigments, antioxidants, flame retardant, and slip additives. In some embodiments of the invention, for example, the method may comprise adding a slip additive to the elastic continuous filaments. The slip additive may be topically applied to the elastic filaments and/or introduced to the elastomeric-polymer melt prior to melt-spinning the elastic continuous filaments. For instance, the slip additive(s) may be melt-dispersed in the elastomeric melt prior to melt-spinning, according to an embodiment of the invention. Without intending to be bound by theory, the slip additive may beneficially reduce the stickiness of the continuous elastic filaments against process surfaces associated with melt-spinning processes. The slip additive, for example, may beneficially reduce (or eliminate) the undesirable breakage of filaments and drips that may be associated with melt-spinning of an elastomeric material. In this regard, exemplary slip additives may bloom rapidly to the surface of the filaments and reduce their coefficient of friction against surfaces found in the process (e.g., wall of the diffuser section, walls of the draw unit, compression rolls, etc.), therefore allowing continuous production of the elastic nonwoven layer(s) with a minimum amount of defects due to break in the elastic continuous filaments.

Exemplary, but non-limiting examples of, slip additives according to certain embodiments of the invention, may comprise one or more of the following: oleamide, erucamide, stearamide, ethylene-bis-oleamide, strearyl erucamide, oleyl palmitamide, bis-stearamide, epoxy functionalized polysiloxane, silicon compounds (e.g., silanes and silicone polymers, including silicone oils, polydiniethylsiloxane, amino-modified polydimethylsiloxane, etc.), and salt derivatives of aromatic or aliphatic hydrocarbon oils (e.g., metal salts of fatty acids, including calcium stearate, zinc stearate, etc.).

In certain embodiments of the invention, as noted above, the elastic continuous filaments may comprise a slip additive, for example added to the elastomeric-polymer melt, in an amount effective to reduce the tendency of the elastic continuous filaments to cling to process surfaces. In some exemplary embodiments, for instance, the elastic continuous filaments may comprise a slip additive(s) comprising from about 0.1 wt. % to about 10 wt. %, based on the total weight of the elastic continuous filaments forming the at least one elastic nonwoven layer. In an embodiment of the invention, the elastic continuous filaments may comprise a slip additive(s) comprising from about 0.1 wt. % to about 5 wt. %, based on the total weight of the elastic continuous filaments forming the at least one elastic nonwoven layer. In certain embodiments of the invention, the elastic continuous filaments may comprise a slip additive(s) comprising from at least about any of the following: 0.05, 0.1, 0.2, 0.3, 0.5, 1, and 2 wt. % and/or at most about 20, 15, 12, 10, 9, 8, 7, 6, and 5 wt. % (e.g., 0.1-2 wt. %, 1-20% , etc.) based on the total weight of the elastic continuous filaments forming the at least one elastic nonwoven layer.

Figure 3:
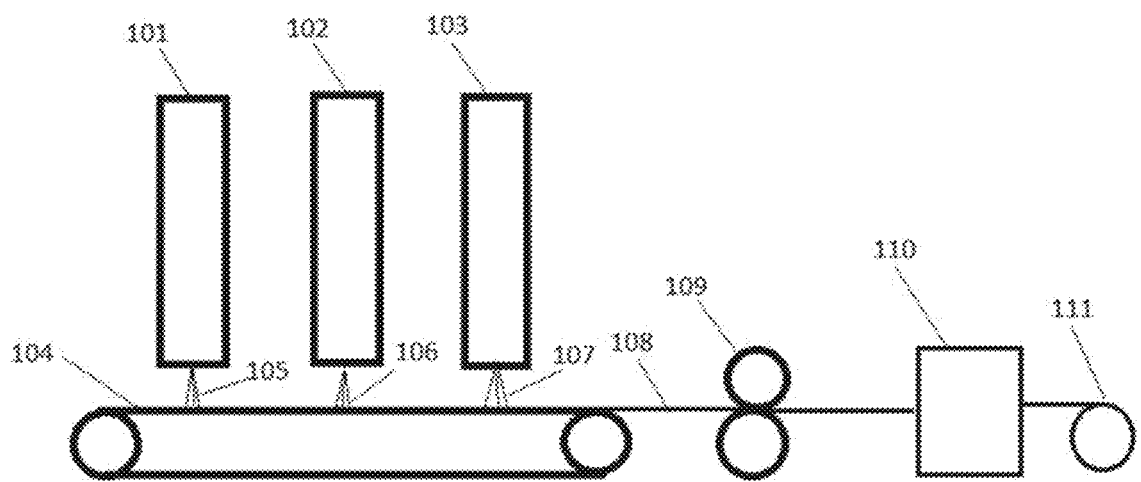
FIG. 3 illustrates a schematic of a process that may be utilized to produce nonwoven composites according to certain exemplary embodiments of the invention.
Figure 2:
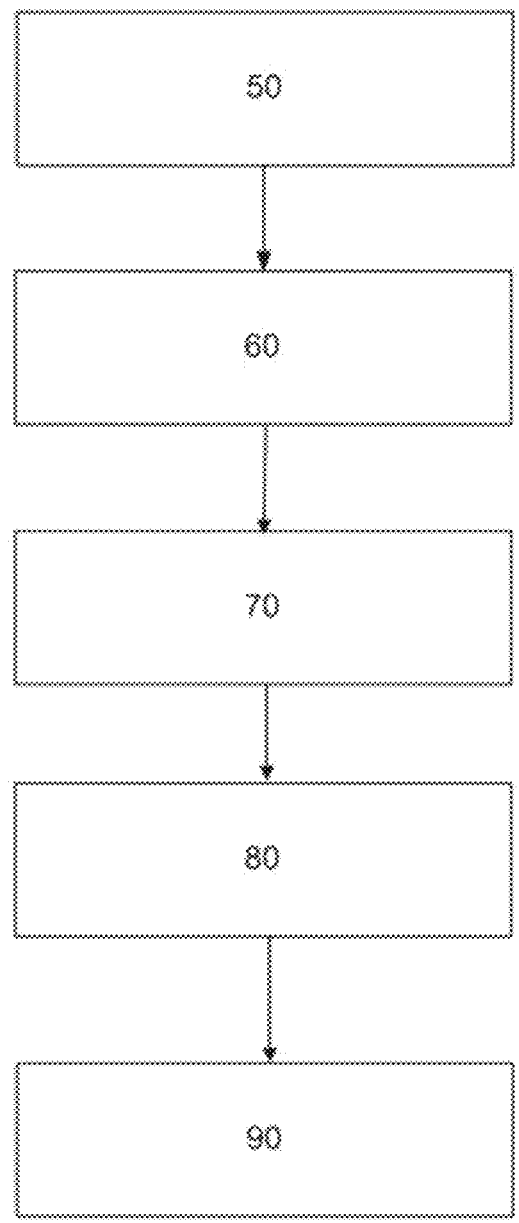
FIG. 2 illustrates a process flow diagram for forming composites according to certain embodiments of the invention.

FIG. 2 illustrates a process flow diagram for forming composites according to certain embodiments of the invention. The methods illustrated by FIG. 2, for example, include a step of forming a first extensible nonwoven layer comprising a first group of extensible filaments 50 and depositing a plurality of elastic continuous filaments directly or indirectly onto the first extensible nonwoven layer to form an elastic nonwoven layer 60. Embodiments illustrated by FIG. 2 also comprise a step of depositing a second extensible nonwoven layer comprising a second group of extensible filaments directly or indirectly onto the elastic nonwoven layer 70. FIG. 2 also illustrates optional steps of bonding the composite 80 and activating the composite 90, such as by an incremental stretching process FIG. 3 illustrates a schematic of a process that may be utilized to produce nonwoven composites according to certain exemplary embodiments of the invention. For instance, FIG. 3 illustrates a spunbond process having three layers of continuous filaments including a first layer of extensible non-elastic filaments 105 that are produced by a first beam 101 and disposed on a moving surface 104. As illustrated in FIG. 3, a layer of elastic continuous filaments 106 is produced from a second beam 102 and is collected on the moving surface on top of the first layer of extensible non-elastic filaments 105. Finally, another layer of extensible non-elastic filaments 107 is produced by a third beam 103 and collected on the moving surface on top of the layer of elastic continuous filaments 106.

The resulting layered composite 108 may then be subjected to a bonding process 109 (e.g., thermal bonding process). As illustrated in FIG. 3, the bonding process may be performed with a calender comprising a heated smooth or anvil roll and another heated roll with a raised pattern, the pattern comprising a plurality of raised protrusions that define a bonding area as previously described. The bonded composite may then be subjected to an activation step 110. As shown in FIG. 3, the composite may be activated in-line with its production or, in a separate operation by using an incremental stretching unit 110 that stretch the extensible filaments 105 and 107 in discrete areas. During the activation step, the layer of elastic continuous filaments 106 also get stretched, however due to the elastic nature of these filaments 106 they recover to be close their original dimensions. The activated nonwoven can be wound onto an uptake roll 111. In this regard, certain embodiments provide a single-step process for forming a composite as disclosed herein.

As a person of ordinary skill in the art would understand having the benefit of this disclosure, the process for manufacturing a composite elastic nonwoven fabric of the invention may comprise any number of beams to dispose any number and types of continuous filament layers to form the composite. Although FIG. 3 illustrates only three (3) spinning beams, it should be understood that the composites disclosed herein may be produced with more than three (3) spinning beams. In certain embodiments of the invention, the method may comprise multiple spinning beams to form a plurality of extensible nonwoven layers defining outer layers having one or more elastic nonwoven layers disposed in between. The extensible nonwoven layers, according to certain embodiments of the invention, may be formed of extensible filaments produced according to the S-TEX™ process owned by Polymer Group Inc., in which a blend of olefin polymers is extruded in a spunbond process and the filaments are drawn at a speed that is lower than typically experienced in a typical spunbond process. This combination of low filament draw and formulation can produce filaments that can be formed into a bonded nonwoven and stretched substantially by an activation process without suffering significant filament breaks.

While certain embodiments of the invention have been described using formulations primarily based on polyolefin polymers, it should be understood that polymers contemplated for use in embodiments of the invention include other families of polymers (e.g., polyester and co-polyester) that can be used to produce elastic and extensible non-elastic filaments that can be formed as discrete layers and bonded together.

EXAMPLES

The present disclosure is further illustrated by the following examples, which in no way should be construed as being limiting. That is, the specific features described in the following examples are merely illustrative and exemplary and should not be construed to be limiting.

I. Formation of Samples and Comparison Samples

Six (6) different composite nonwovens (i.e., Samples 1, 2, 3, 4, 5, and 6 as referenced herein) were made on a three-beam spunbond line. That is, the three-beam spunbond line includes a first beam, a second beam, and a third beam. For each sample, the first and third beams were used to produce the outer layers (e.g., comprising extensible non-elastic filaments according to these exemplary embodiments) of the composite. In particular, each of the first and third beams was set to produce high elongation continuous filaments (e.g., extensible non-elastic filaments) while using a formulation that consisted of (i) 75.25 wt. % of a narrow molecular weight homopolymer polypropylene typically used for spunbond production and having a MFR of 25 g/10 min when tested as per ISO 1133 at 230° C. and under a load of 2.16 kg, (ii) 20 wt. % of a reactor grade thermoplastic copolymer polyolefin having a MFR of 27 g/10 min and made using the LyondellBasell proprietary Catalloy process, (iii) 4 wt. % of a polyethylene fiber grade resin having a MFR of 17 g/min when tested at 190° C. under a load of 2.16 kg, and (iv) 0.75 wt. % of a polypropylene based masterbatch containing 40% of a titanium dioxide pigment. The second beam (i.e., the middle beam) was set to produce the middle layer of filaments (e.g., elastic continuous filaments) using a blend consisting of 97 wt. % VISTAMAXX™ VM 7050, which is commercially available from ExxonMobil Chemical Company, and 3 wt. % of a commercially available slip additive for polypropylene sold by Polyvel Inc., Hammonton, N.J. USA under the name S-1519. The slip additive was added to reduce the tendency of the filaments from sticking to surfaces of the production line. It is believed that the slip additive blooms rapidly to the surface of the melt-spun filaments, therefore reducing their coefficient of friction against surfaces, such as the walls of the diffuser located just prior to collection of the filaments on the collection belt.

The three (3) layered webs of Samples 1 to 6 were then collected from the collection belt and thermally bonded with a hot calender fitted with a smooth anvil roll and an embossed roll, the latter having a diamond pattern that bonds the nonwoven on about 12% of its surface. Temperatures and pressures were selected to produce good bond strength. For the production of these samples, the melt temperature targeted for the beam 1 and 3 was 235° C., while for beam 2 it was 212° C. Throughputs and draw forces were selected to produce extensible filaments in beams 1 and 3 while maintaining stable spinning condition for all beams.

The bonded Samples were activated in a separate operation using the MICROSPAN® stretching process developed by Biax-Fiberfilm Corporation, Greenville Wis. This process uses two sets of closely spaced disks that are engaged in each other. By passing the web in the nip point formed by those two sets of disks, the nonwoven becomes activated by stretching it in the CD direction. For Samples 1 to 5, the spacing between the disks and the engagement of one set of disks relative to the other set was selected to optimize the elastic properties for the activated nonwoven. For Sample 6, the same precursor fabric as used for Sample 2 was utilized; however a lesser engagement of the disks was used to produce a lower level of activation for this sample.

In Table 1 the basis weights of the samples and the process conditions utilized for producing Samples 1 to 6 have been provided.

TABLE 1

Production of the spunbond precursors for the samples 1 to 6

| Sample | Nominal basis weight for the spunbond prior to activation | | | | Calender set point | |
|---|---|---|---|---|---|---|
| | total basis weight gsm | Basis weight layer 1 gsm | Basis weight layer 2 gsm | Basis weight layer 3 gsm | Temperature roll 1/2 ° C. | Linear pressure N/mm |
| 1 | 120 | 30 | 60 | 30 | 128/128 | 30 |
| 2 | 120 | 30 | 60 | 30 | 128/128 | 60 |
| 3 | 120 | 25 | 70 | 25 | 128/128 | 30 |
| 4 | 90 | 23 | 45 | 23 | 133/133 | 60 |
| 5 | 77 | 16 | 45 | 16 | 128/128 | 30 |
| 6 | 120 | 25 | 70 | 25 | 128/128 | 60 |

Without intending to be bound by theory, nonwovens, such as Sample 6, may not be as desirable according to certain embodiments of the invention due to the much higher strength needed to stretch them at 100%. The load at 50% is not significantly higher than for the other samples, therefore resulting into a high Load Ratio. In certain embodiments, for example, a Load Ratio comprising less than 30 or even less than 15 may be considered desirable and more preferred, according to certain embodiments of the invention.

Comparative Samples 7, 8 and 9 were produced by blowing 50, 60 or 70 gsm of meltblown fiber made from VISTAMAXX™ VM7050 on a 30 gsm extensible non-elastic nonwoven known as SOFTSPAN® (e.g., comprising a blend of polypropylene, a copolymer of polypropylene, a polyethylene and a white pigment) and sold by Polymer Group Inc. An additional 30 gsm SOFTSPAN® web was added on top of the layer of VISTAMAXX™ VM7050 and the composites were thermally bonded using a point bond calender. The resulting composites were also each activated using the MICROSPAN® stretching process. The meltblown fibers for Samples 7, 8 and 9 were produced on a meltblown line made by Biax-Fiberfil Corporation.

Comparative Sample 10 was manufactured similar to that of Comparative Sample 8 with the exception that less disk engagements were used, producing a lower degree of activation for Comparative Sample 10. Without intending to be bound by the theory, elastic nonwovens manufactured in this manner are generally considered less desirable because of the high force needed to stretch the sample by 100% with no equivalent increase in load at 50% stretch, as illustrated by the higher Load Ratio.

A commercially available comparative composite, namely Comparative Sample 11, consisted of a sample made from two extensible thermally bonded carded nonwovens adhesively bonded to an elastic film. Upon examination it appeared that this composite having a nonwoven/film/nonwoven structure had also been activated with what appears to be a CD incremental stretching. The basis weight of this composite in the relaxed state was found to be 123 gsm.

A commercially available comparative composite, namely Comparative Sample 12, consisted of an elastic film with a nonwoven adhered to it on each side. The composite also appeared to have been activated in order to have high elongation in the CD direction. The basis weight of this composite in the relaxed state was found to be about 105 gsm.

A commercially available comparative composite, namely Comparative Sample 13, consisted of an elastic film disposed between two extensible nonwovens; the nonwovens having the appearance of spunbond fabrics. This composite appeared to have been thermally bonded. The basis weight of this composite in the relaxed state was found to be 118 gsm.

II. Air Permeability

Air permeability measurements were conducted for Samples 2, 3, and 6 as well as Comparative Samples 7, 8, 9, 10, 13. The results from these air permeability measurements are summarized in Table 2. The air permeability results shown in Table 2 clearly illustrate that higher permeability values may be achieved when the elastic fiber layer is made by the spunbond or meltblown process in comparison to composites comprising a film.

TABLE 2

Air permeability comparison for Samples after activation and at relaxed state

| Sample of activated laminate or spunbond | Air permeability m³/m²/min |
| --- | --- |
| Sample 2 (60 gsm elastic filaments) | 32 |
| Sample 3 (70 gsm elastic filaments) | 76 |
| Sample 6 (60 gsm elastic filament-activation not optimized) | 32 |
| Comp. Sample 7 (50 gsm elastic MB fibers) | 67 |
| Comp. Sample 8 (60 gsm elastic MB fibers) | 39 |
| Comp. Sample 9 (70 gsm elastic MB fibers) | 23 |
| Comp. Sample 10 (60 gsm elastic MB fibers-activation not optimized) | 20 |
| Comp. Sample 13 | 0 |

III. Elastic Properties

For many elastic composites/fabrics, it is generally accepted that it is preferred the initial force needed to stretch the fabric at 100% elongation not be particularly high because this is representative of the force needed to be applied by the user while installing or using the product (e.g. fitting a diaper on a child). For such products (e.g., elastic composites/fabrics) it may also be preferred that the force exerted by the product at 50% elongation be maximized as this is the force exercised by the composite to keep the product in place. For instance, in the case of elastic tabs on a diaper, the first stretch at 100% models the force exerted by the parent to stretch the elastic to secure the tabs to the front of the diaper, while the force at 50% models the force exerted by the tab to keep the diaper secured tight against the wearer. If the force at 50% is too low, for example, movements from the wearer may allow the diaper to slip and not remain in place. It may often also be desirable that the force needed to stretch the sample a second time at 100% not be substantially different from the first time the fabric is stretched, as this may be part of the overall consumer experience.

Table 3 summarizes elastic properties of the samples and comparative examples. The results summarized in Table 3 illustrate that Samples 1, 2, 3, 4, 5, and 6 (made with continuous elastic filaments), as well as Comparative Examples 7, 8, 9 and 10 (made with meltblown elastic filaments) achieved from cycle to cycle good retention of the load at 100% and 50% stretch. However, the results also show that for a given weight of fabric or a given weight of the layer of elastic fiber, Samples 1 to 5, in general, performed better than, for example, Comparative Samples 7 to 9 in regard to Load Ratio.

The results from Table 3 also show that activation of a sample can have an impact on the load at 100% or on the Load Ratio. This impact, for example, is well illustrated by the high load at 100% or high Load Ratio for the lower activation Sample 6 and 10 when compared to their high activation equivalent samples.

TABLE 3

Test results for Samples and Comparative Samples after activation

CD stress retention as per modified ASTM D-5459-95 test method

| Sample | Actual basis weight at relaxed state gsm | CD Force for first cycle at 100% elongation g/25 mm | CD Force for first cycle at 50% elongation g/25 mm | CD Force for second cycle at 100% elongation g/25 mm | CD Force for second cycle at 50% elongation g/25 mm | CD Force for third cycle at 50% elongation g/25 mm | CD Permanent Set after 1ˢᵗ cycle % | CD Load Ratio |
| --- | --- | --- | --- | --- | --- | --- | --- | --- |
| 1 | 108 | 711 | 73 | 678 | 73 | 69 | 16.5 | 9.7 |
| 2 | 111 | 750 | 81 | 719 | 76 | 75 | 17.3 | 9.3 |
| 3 | 112 | 1074 | 76 | 1030 | 72 | 68 | 22.5 | 14.1 |
| 4 | 84 | 503 | 50 | 478 | 48 | 46 | 19 | 10.0 |
| 5 | 73 | 371 | 54 | 353 | 51 | 50 | 16.9 | 6.9 |
| 6 | 112 | 2040 | 64 | 1954 | 60 | 58 | 25.2 | 31.9 |
| 7 | 92 | 1040 | 41 | 999 | 36 | 36 | 24.8 | 25.4 |
| 8 | 105 | 908 | 64 | 863 | 59 | 59 | 20.0 | 14.1 |
| 9 | 112 | 1226 | 91 | 1180 | 86 | 82 | 18.8 | 13.4 |
| 10 | 111 | 2497 | 64 | 2360 | 59 | 54 | 26.3 | 39 |
| 11 | 118 | 426 | 109 | 390 | 109 | 104 | 8.3 | 3.9 |
| 12 | 105 | 1037 | 125 | 1008 | 119 | 118 | 14.8 | 8.3 |
| 13 | 123 | 1166 | 113 | 1117 | 104 | 100 | 16.5 | 10.3 |

While it can be expected that the activation process may cause a reduction in basis weight by producing some permanent deformation in the fabric, it was observed that the samples in which the elastic layer consisted of elastic continuous filaments had a basis weight in the relaxed state that is closer to the nominal basis weight calculated from the line throughput than those calculated for the Comparative Samples 7 to 9 where the elastic middle layer is made up of elastic meltblown fibers. Without intending to be bound by the theory, it is believed that the foregoing difference is related to the catastrophic failure or holes observed with the samples (e.g., Comparative Examples) where elastic meltblown fibers are used.

Figure 4:
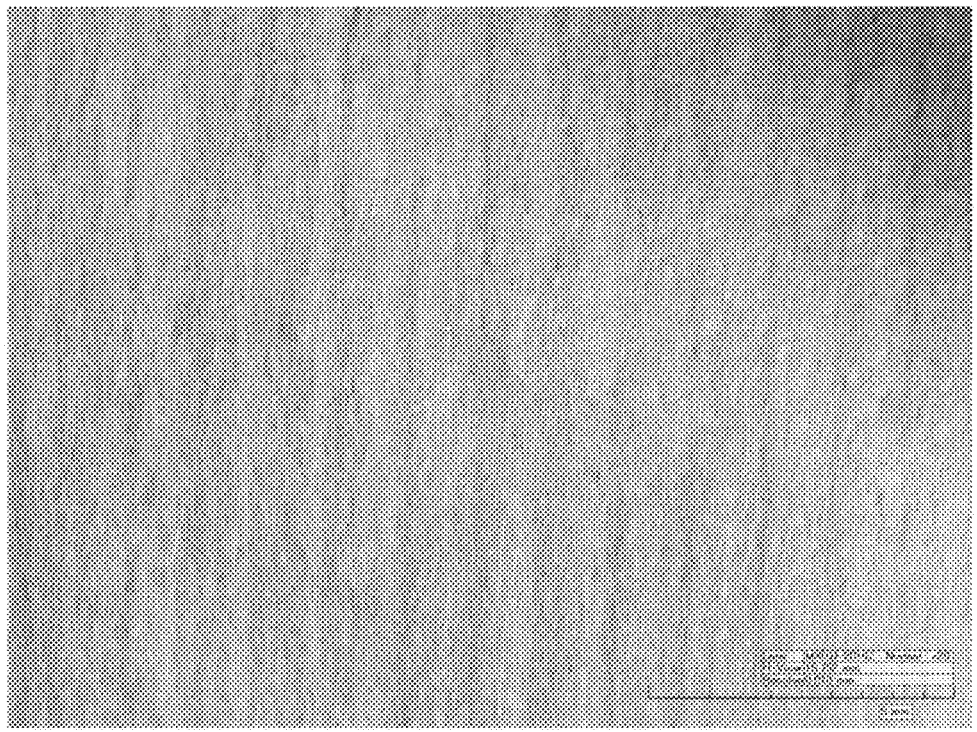
FIG. 4 shows a Comparative Sample while in a relaxed state.
Figure 5:
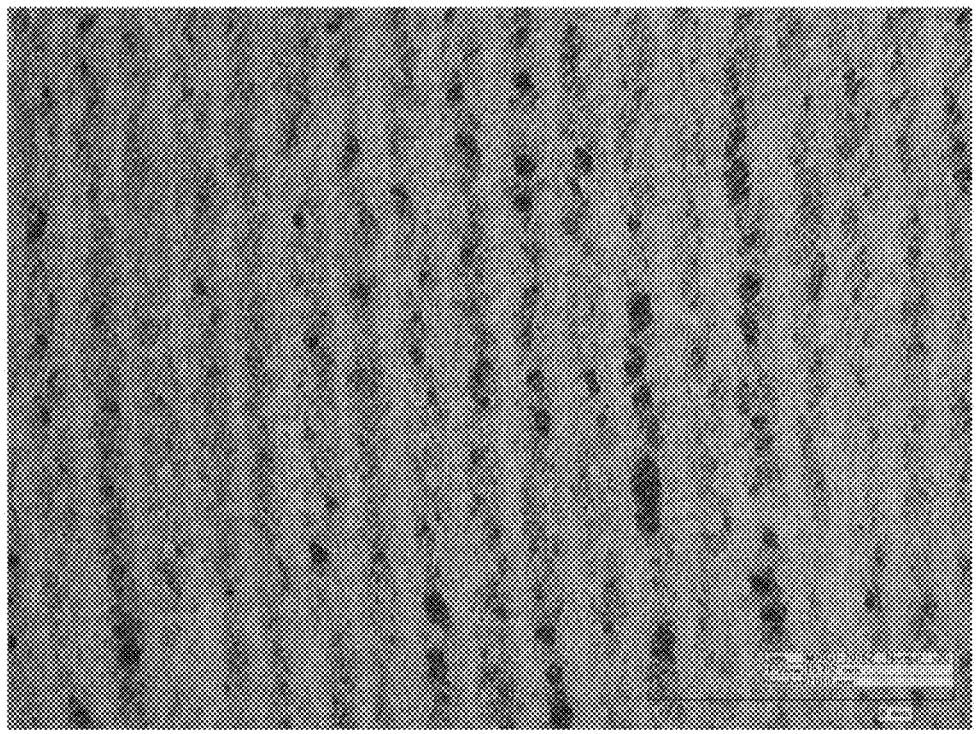
FIG. 5 shows the Comparative Sample of FIG. 4 while in a 50% stretched state.
Figure 6:
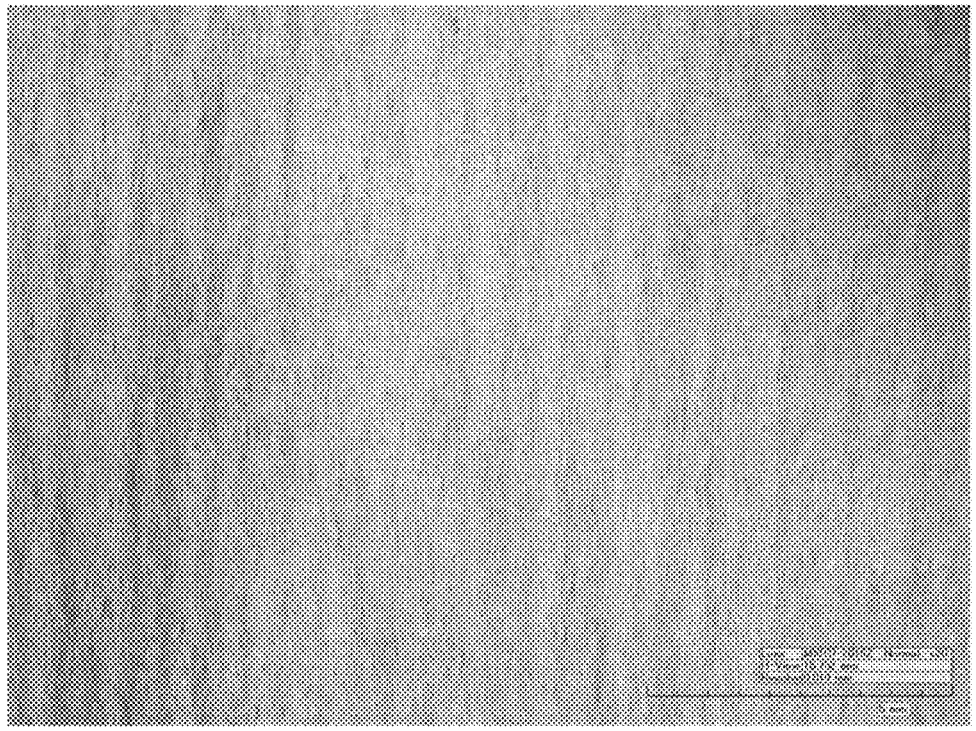
FIG. 6 shows another Comparative Sample while in a relaxed state.
Figure 7:
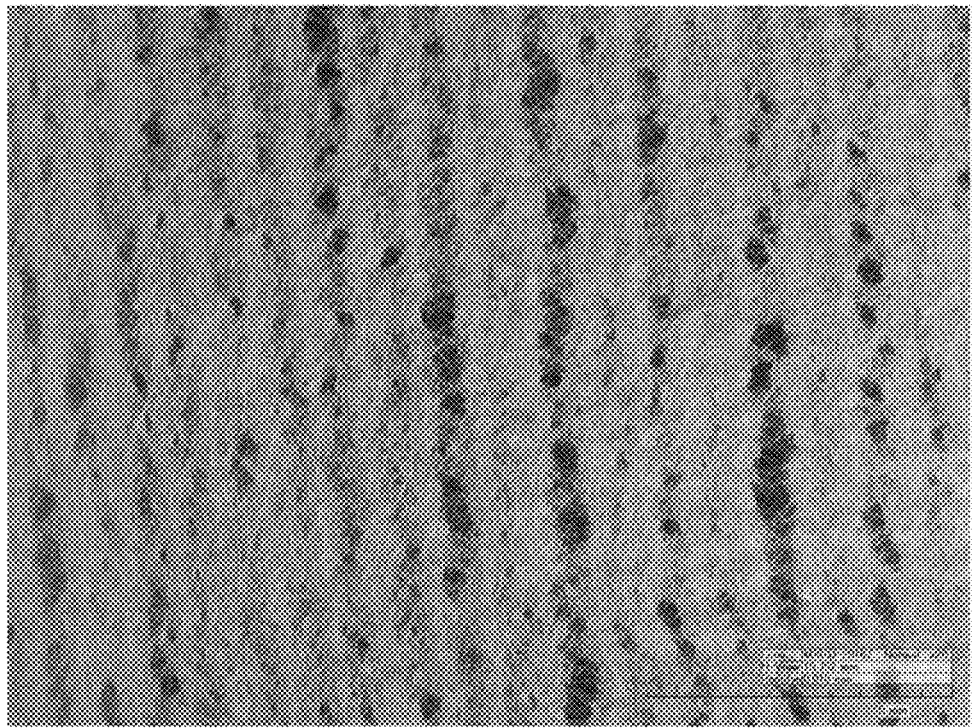
FIG. 7 shows the Comparative Sample of FIG. 6 while in a 50% stretched state.
Figure 8:
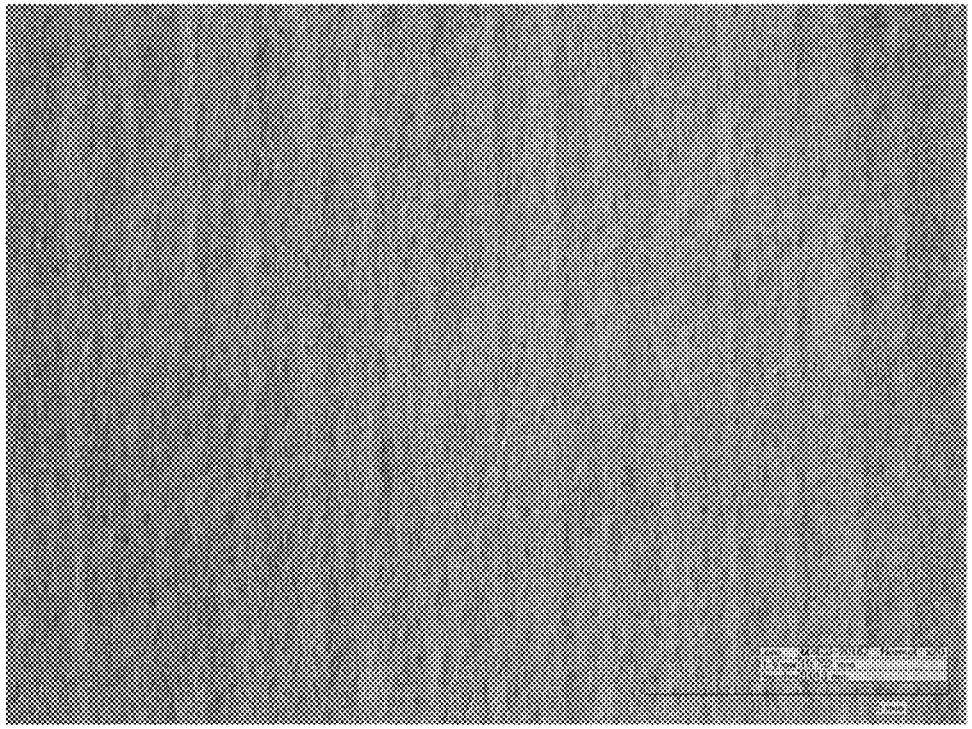
FIG. 8 shows yet another Comparative Sample while in a relaxed state.
Figure 9:
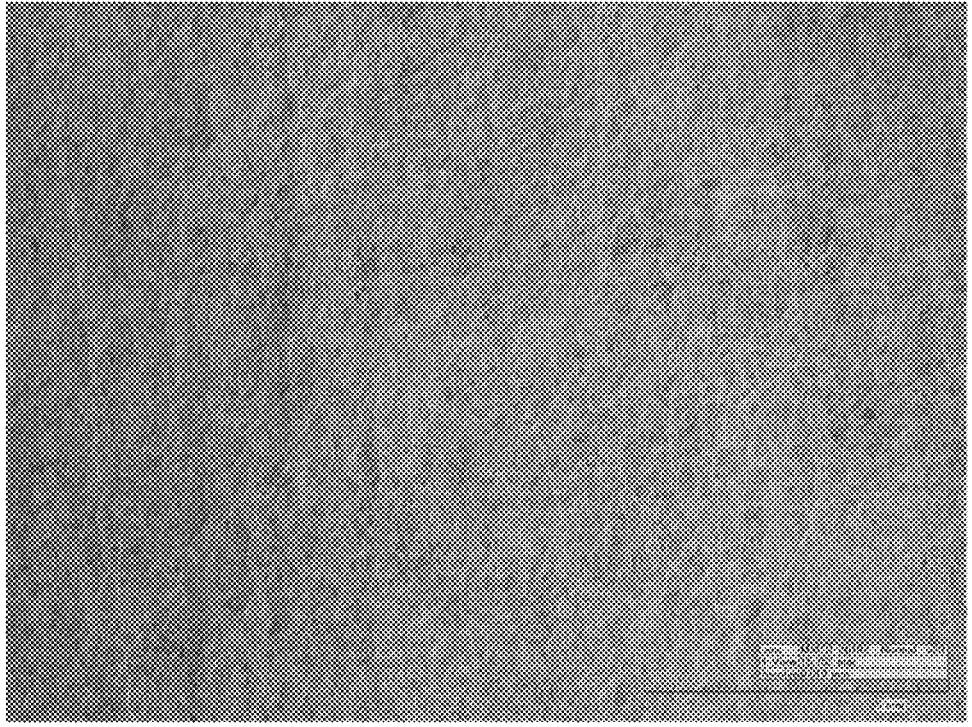
FIG. 9 shows the Comparative Sample of FIG. 8 while in a 50% stretched state.
Figure 10:
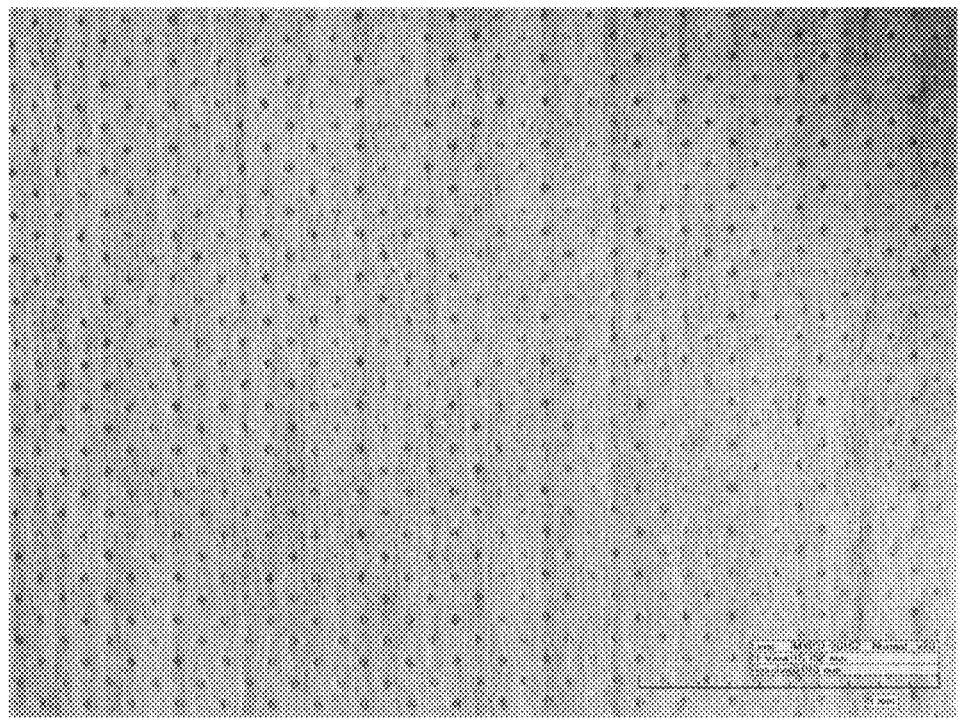
FIG. 10 shows an exemplary embodiment of the invention while in a relaxed state.
Figure 11:
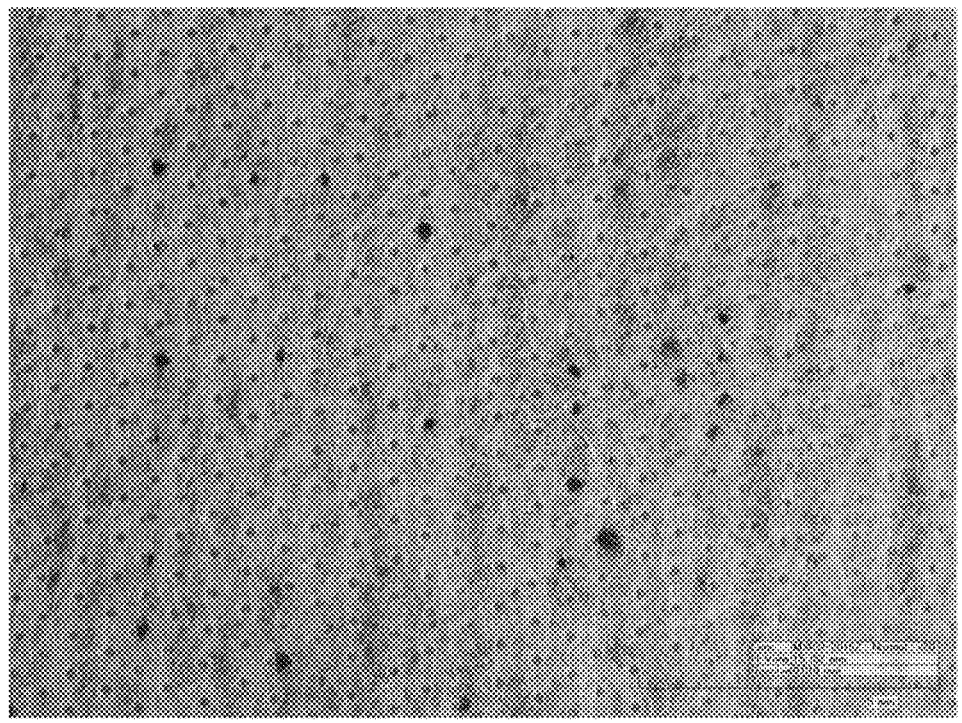
FIG. 11 shows the exemplary embodiment of FIG. 10 while in a 50% stretched state.
Figure 12:
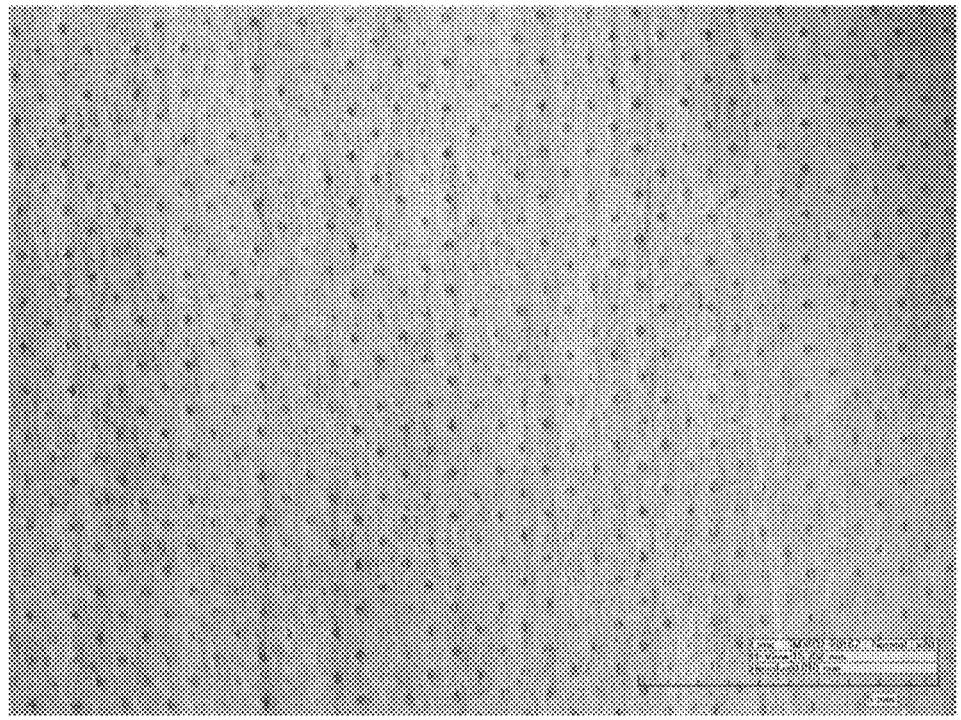
FIG. 12 shows another exemplary embodiment of the invention while in a relaxed state.
Figure 13:
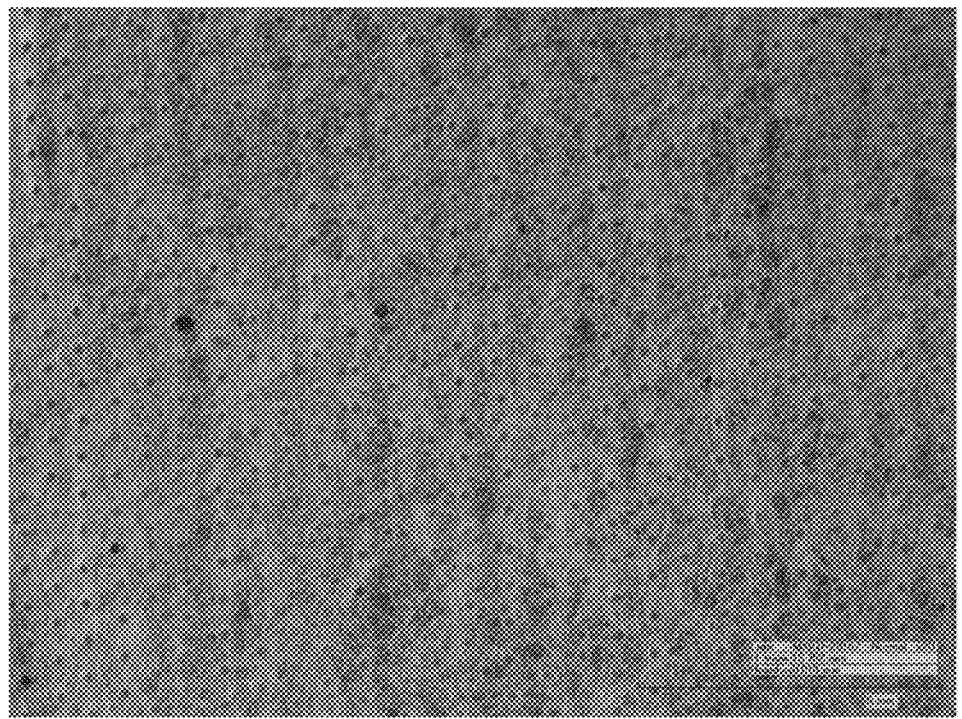
FIG. 13 shows the exemplary embodiment of FIG. 12 while in a 50% stretched state.
Figure 14:
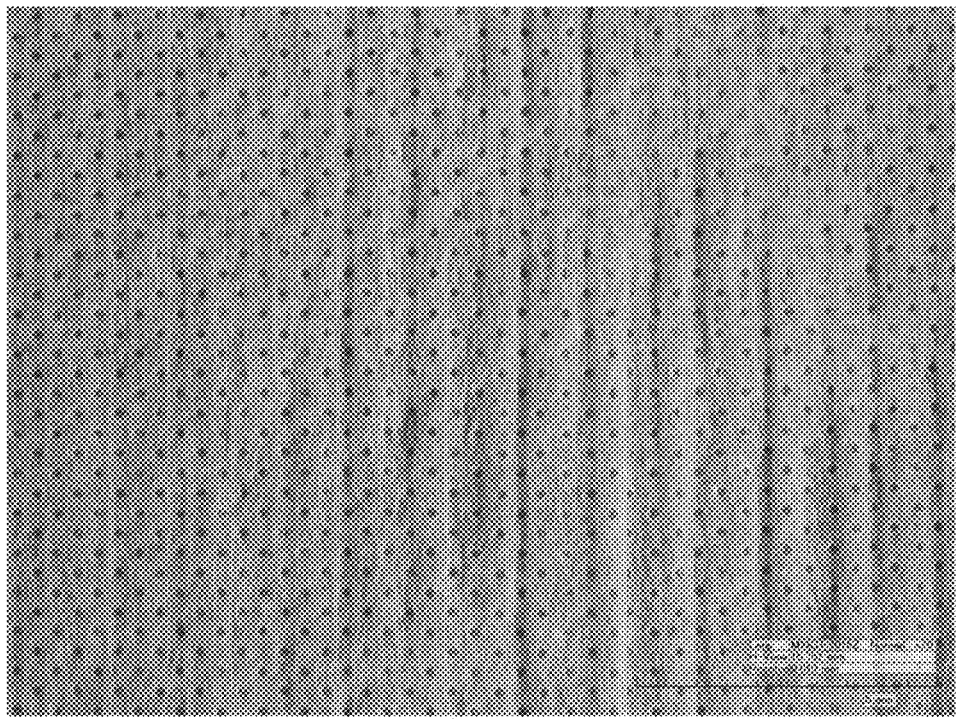
FIG. 14 shows yet another exemplary embodiment while in a relaxed state.

An additional difference noted between the samples comprising continuous elastic filaments rather than meltblown elastic fibers is the appearance of the activated product. The difference in visual appearance is well illustrated in FIGS. 4-15, particularly when considered in view of the data illustrated in Table 3. In particular, FIG. 4 shows Comparative Sample 7 (contains elastic meltblown fibers) in a relaxed state, while FIG. 5 shows Comparative Sample 7 stretched at 50%. Similarly, FIG. 6 shows Comparative Sample 8 (contains elastic meltblown fibers) in a relaxed state, while FIG. 7 shows Comparative Sample 8 stretched at 50%. FIG. 8 shows Comparative Sample 10 (contains elastic meltblown fibers) in a relaxed state, while FIG. 9 shows Comparative Sample 8 stretched at 50%. FIG. 10 shows Sample 2 (continuous elastic filaments) in a relaxed state, while FIG. 11 shows Sample 10 stretched at 50%. FIG. 12 shows Sample 3 (continuous elastic filaments) in a relaxed state, while FIG. 13 shows Sample 2 stretched at 50%. FIG. 14 shows Sample 6 (continuous elastic filaments) in a relaxed state, while FIG. 14 shows Sample 6 stretched at 50%.

Comparative Samples 7 and 8 appear to have been activated in a way that produces an acceptable Load Ratio or low load at 100% stretch. However, FIG. 5 (Comparative Sample 7) and 7 (Comparative Example 8) highlight how each of these comparative samples at 50% stretch show significant formation of holes that have been created during the activation process and how visible these holes are when the product is stretched. For Comparative Sample 10, which had been less activated, the appearance at 50% stretch is much better. However, Comparative Sample 10 also exhibits a high Load Ratio or a high load at 100% stretch. This high load at 100% stretch or high Load Ratio is less desirable and shows the need to use high activation for this type of sample. While not intending to be limited to the following theory, it is believed that the weakness of the individual meltblown fibers result in more breaks when stretched during the activation process.

Figure 15:
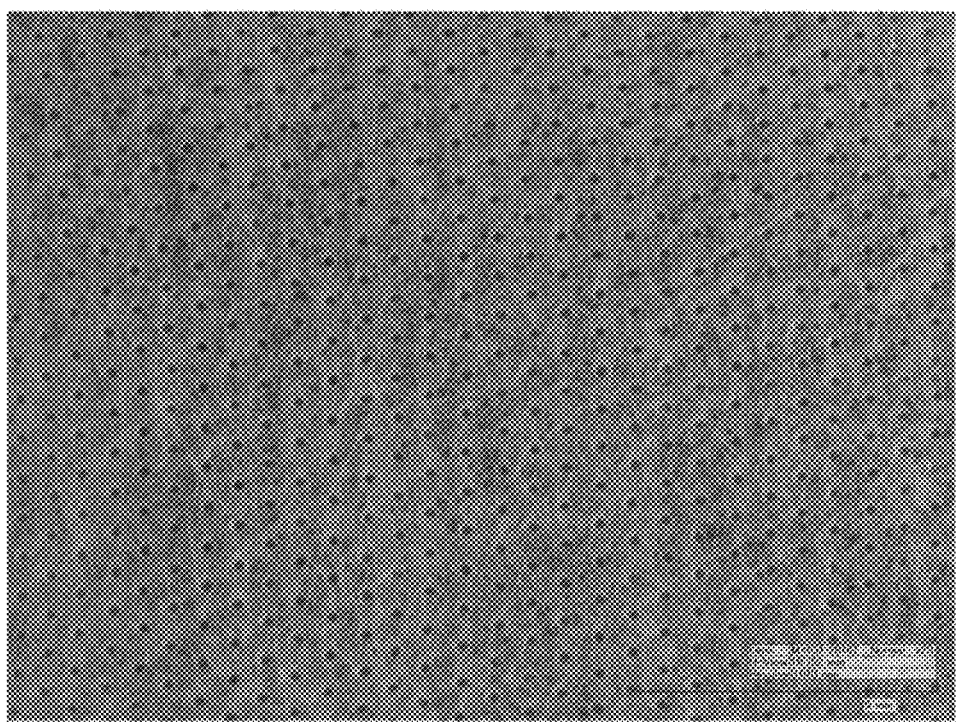
FIG. 15 shows the exemplary embodiment of FIG. 14 while in a 50% stretched state.

In contrast, Samples 2 and 3, which were each produced at high activation and exhibited relatively low Load Ratio or load at 100% stretch, exhibited a noticeably better appearance than the Comparative Samples. For instance, the activated fabric stretch at 50% for Samples 2 and 3 were visually good (as shown in FIGS. 11 and 13) and showed very few defects. As such, these samples should be viewed more favorably by the user. Without intending to be bound by theory, it is believed that the larger diameter of the continuous elastic filaments in Samples 2 and 3, for example, and the likely greater orientation of the polymer in the continuous filaments produce fibers with higher tenacity than meltblown fibers. Therefore, less holes are formed during activation for these nonwoven composites (e.g., Samples 2 and 3). FIGS. 14 and 15 show Sample 6, which was produced at a lower level of activation. While the appearance of Sample 6 when stretched at 50% is very good, this sample also exhibits a high Load Ratio or load at 100% stretch.

Finally, the nonwoven composites according to certain embodiments of the invention were very drapable and soft, offering a pleasant hand to the user.

IV. Opacity

The opacities of the selected samples were measured in the relaxed state and at 50% stretch. The results of these measurements are summarized in Table 4.

TABLE 4

Opacity results for Samples after activation

| Sample | Opacity of Sample in relaxed state % | Opacity of Sample at 50% Stretch % |
|---|---|---|
| 2 | 60.5 | 52.5 |
| 3 | 58 | 48.5 |
| 4 | 54.5 | 40 |
| 5 | 47 | 38.5 |
| 7 | 54.5 | 42.5 |
| 8 | 53.5 | 43.5 |

V. Test Methods

Air permeability data were produced using a TexTest FX3300 Air Permeability Tester manufactured by TexTest AG of Zurich, Switzerland. The TexTest FX3300 Air Permeability Tester was used in accordance with the manufacturer's instructions using a 38 cm$^2$ orifice and a pressure drop of 125 Pa as per test method WSP 70.1. The results were recorded in the units of m$^3$/m$^2$/min.

Elastic properties of the samples were measured as per a modified version of the standard test method ASTM D 5459-95 "Machine Direction Elastic Recovery and Permanent Deformation and Stress Retention of Stretch Wrap Film". The first modification was that the initial grip separation was reduced to 12.7 mm (0.5 in). A second modification was that the rate of grip separation was reduced to 50.8 mm/min (2 in/min). A third modification was that the samples were 25.4 mm wide by 76.2 mm long (1 in×3 in) and, a fourth modification was that the samples were tested only in the CD direction. A fifth modification was to include the Load Ratio in the reported result. This Load Ratio consisted of ratio of the load measured during the first cycle while the stretch is at 100% and the load measured during the first cycle when the stretch is reduced to 50%.

Opacity was measured by standard test method WSP 60.1. For the samples in a relaxed state, a single layer of the sample was deposited on the black tile prior to measurement. For the samples at 50% stretch, the samples were stretched in the CD direction by 50% of their original dimension and were kept in this state during measurement with the black tile backing.

Appearance of the samples at a relaxed state or 50% elongation were taken using a Hirox KH7700 microscope system (Hirox Co. Ltd., Tokyo, Japan).

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A nonwoven composite, comprising:
   (a) at least one extensible nonwoven layer, including a first extensible nonwoven layer comprising a first plurality of extensible spunbond filaments;
   (b) at least one elastic spunbond nonwoven layer, said at least one elastic spunbond nonwoven layer having monocomponent elastic continuous filaments; wherein the monocomponent elastic continuous filaments comprise a propylene-ethylene elastomeric copolymer, a polyether block amide copolymer, a copolyester thermoplastic elastomer, or a thermoplastic urethane elastomer;

(c) a second extensible nonwoven layer comprising a second plurality of extensible spunbond filaments; wherein said at least one elastic spunbond nonwoven layer is directly or indirectly positioned between the first extensible nonwoven layer and the second extensible nonwoven layer, and (d) a plurality of thermal point bonds that extend through the first extensible nonwoven layer, the at least one elastic spunbond nonwoven layer, and into the second extensible nonwoven layer, and wherein the plurality of thermal point bonds define a bonding pattern for each of the nonwoven composite, the first extensible nonwoven layer, the at least one elastic spunbond nonwoven layer, and the second extensible nonwoven layer, and wherein the bonding pattern consists of the plurality of thermal point bonds, wherein at least the first plurality of extensible filaments comprise permanent deformations associated with incremental stretching, and the at least one elastic spunbond nonwoven layer comprises from 50% to 85% by weight of the nonwoven composite.

2. The composite according to claim 1, wherein the at least one spunbond elastic nonwoven layer comprises a slip additive.

3. The composite according to claim 2, wherein the slip additive comprises from about 0.1 wt % to about 5 wt %, based on the total weight of the monocomponent elastic continuous filaments forming the at least one elastic spunbond nonwoven layer.

4. The composite according to claim 1, wherein at least one of the first extensible nonwoven layer and the second extensible nonwoven layer comprises an extensible non-elastic filament.

5. The composite according to claim 1, wherein the composite comprises a Load Ratio in a first direction comprising less than about 30; wherein the Load Ratio is a ratio of (i) a first load required to stretch the composite to a first-stretched length of 100% of an original and non-stretched length and (ii) a second load required to stretch the composite to a second-stretched length of 50% of the original and non-stretched length.

6. The composite according to claim 5, wherein the Load Ratio comprises from about 5 to about 15.

7. A method for producing a nonwoven composite, comprising:
(a) depositing a first group of extensible spunbond filaments from a first beam onto a moving surface, wherein the first group of extensible spunbond filaments define a first extensible nonwoven layer;
(b) depositing a plurality of monocomponent elastic continuous filaments directly onto the first extensible nonwoven layer to form an elastic spunbond nonwoven layer from a second beam; wherein the monocomponent elastic continuous filaments comprise a propylene-ethylene elastomeric copolymer, a polyether block amide copolymer, a copolyester thermoplastic elastomer, or a thermoplastic urethane elastomer;
(c) depositing a second group of extensible spunbond filaments from a third beam directly onto the elastic spunbond nonwoven layer, wherein the second group of extensible spunbond filaments define a second extensible nonwoven layer;
(d) thermally bonding the first extensible nonwoven layer, the elastic spunbond nonwoven layer, and the second extensible nonwoven layer together via a plurality of thermal point bonds to form a pre-activated composite; and
(e) activating the pre-activated composite to form the nonwoven composite by incrementally stretching the pre-activated composite; wherein incrementally stretching of the pre-activated composite permanently elongates the first group of extensible fibers and the second group of extensible fibers;

wherein the elastic spunbond nonwoven layer comprises from 50% to 85% by weight of the composite; and wherein the plurality of thermal point bonds extend through the first extensible nonwoven layer, the elastic spunbond nonwoven layer, and into the second extensible nonwoven layer, and wherein the plurality of thermal point bonds define a bonding pattern for each of the nonwoven composite, the first extensible nonwoven layer, the elastic spunbond nonwoven layer, and the second extensible nonwoven layer, and wherein the bonding pattern consists of the plurality of thermal point bonds.

8. The method according to claim 7, wherein the plurality of thermal point bonds defines a bonded area from about 2% to about 30%.

9. The method according to claim 8, wherein the bonded area comprises from about 5% to about 25% of an outer surface of the composite.

10. The method according to claim 7, wherein the first extensible nonwoven layer and the second extensible nonwoven layer each comprises continuous filaments.

11. The method according to claim 7, further comprising forming an elastomeric-polymer melt and melt-spinning the elastomeric-polymer melt to form the plurality of monocomponent elastic continuous filaments.

12. The method according to claim 11, wherein the elastomeric-polymer melt further comprises from about 0.1 wt % to about 5 wt % of a slip additive, based on the total weight of the elastic continuous filaments.

13. The method according to claim 7, wherein at least one of the first extensible nonwoven layer and the second extensible nonwoven layer comprises an extensible non-elastic filament.

14. The method according to claim 7, wherein the composite comprises a Load Ratio in the first direction comprising less than about 30; wherein the Load Ratio is a ratio of (i) a first load required to stretch the composite to a first-stretched length of 100% of an original and non-stretched length and (ii) a second load required to stretch the composite to a second-stretched length of 50% of the original and non-stretched length.

15. The composite according to claim 1, wherein in the monocomponent elastic continuous filaments comprise a copolymer of propylene and ethylene having isotactic polypropylene microcrystalline regions and random amorphous regions.

16. The composite according to claim 1, at least the first plurality of extensible filaments is permanently elongated.

17. The composite according to claim 5, wherein the Load Ratio comprises from about 1 to about 10.

18. The composite according to claim 1, wherein the bonding pattern defines a bonding area, wherein the bonding area comprises from 5 to 25%.

* * * * *

UNITED STATES PATENT AND TRADEMARK OFFICE
CERTIFICATE OF CORRECTION

| | |
|---|---|
| PATENT NO. | : 11,161,321 B2 |
| APPLICATION NO. | : 15/000732 |
| DATED | : November 2, 2021 |
| INVENTOR(S) | : Erlandsson et al. |

It is certified that error appears in the above-identified patent and that said Letters Patent is hereby corrected as shown below:

In the Claims

In Column 22, Line 55, in Claim 15, "The composite according to claim 1, wherein in the" should read --The composite according to claim 1, wherein the--.

Signed and Sealed this
Thirty-first Day of May, 2022

Katherine Kelly Vidal
*Director of the United States Patent and Trademark Office*